United States Patent [19]

Young

[11] Patent Number: 5,391,154

[45] Date of Patent: Feb. 21, 1995

[54] TROCAR SEAL SYSTEM

[75] Inventor: Wayne P. Young, Brewster, N.Y.

[73] Assignee: United States Surgical Corporation, Norwalk, Conn.

[21] Appl. No.: 113,931

[22] Filed: Aug. 30, 1993

[51] Int. Cl.⁶ .............................................. A61M 5/178
[52] U.S. Cl. .................................... 604/167; 604/256; 251/9; 251/149.1
[58] Field of Search ............... 604/167, 256, 164, 264; 251/4, 9, 149.1

[56] References Cited

U.S. PATENT DOCUMENTS

| | | |
|---|---|---|
| 2,797,837 | 7/1957 | Roberts . |
| 3,197,173 | 7/1965 | Taubenheim . |
| 3,473,779 | 10/1969 | Gustafson ................... 251/9 |
| 3,875,938 | 4/1975 | Mellor .................... 604/167 |
| 3,970,089 | 7/1976 | Saice . |
| 3,977,400 | 8/1976 | Moorehead . |
| 4,000,739 | 1/1977 | Stevens . |
| 4,177,814 | 12/1979 | Knepshield et al. . |
| 4,233,982 | 11/1980 | Bauer et al. ............. 604/256 |
| 4,240,411 | 12/1980 | Hosono ..................... 128/4 |
| 4,243,034 | 1/1981 | Brandt . |
| 4,338,934 | 7/1982 | Spademan ............. 604/167 |
| 4,379,458 | 4/1983 | Bauer et al. . |
| 4,424,833 | 1/1984 | Spector et al. ......... 137/849 |
| 4,430,081 | 2/1984 | Timmermans .......... 604/256 |
| 4,512,766 | 4/1985 | Vailancourt ............ 604/169 |
| 4,531,937 | 7/1985 | Yates ....................... 604/53 |
| 4,535,773 | 8/1985 | Yoon ....................... 604/51 |
| 4,569,502 | 2/1986 | Elliott ....................... 251/9 |
| 4,580,573 | 4/1986 | Quinn ..................... 604/169 |
| 4,609,300 | 9/1986 | Robert ..................... 251/9 |
| 4,610,665 | 9/1986 | Matsumoto et al. ..... 604/167 |
| 4,610,674 | 9/1986 | Suzuki et al. ........... 604/282 |
| 4,611,785 | 9/1986 | Steer ....................... 604/256 |
| 4,626,245 | 12/1986 | Weinstein ............... 604/167 |
| 4,629,450 | 12/1986 | Suzuki et al. .......... 604/167 |
| 4,634,432 | 1/1987 | Kocak .................... 604/167 |
| 4,654,030 | 3/1987 | Moil et al. .............. 604/165 |
| 4,655,752 | 4/1987 | Honkanen et al. ..... 604/256 |
| 4,673,393 | 6/1987 | Suzuki et al. .......... 604/167 |
| 4,759,751 | 7/1988 | Gabel et al. ............ 604/256 |
| 4,798,594 | 1/1989 | Hillstead ................ 604/167 |

(List continued on next page.)

FOREIGN PATENT DOCUMENTS

| | | |
|---|---|---|
| 29864 | 6/1981 | European Pat. Off. . |
| 054728 | 6/1982 | European Pat. Off. . |
| 0150666 | 8/1985 | European Pat. Off. . |
| 0323018 | 7/1989 | European Pat. Off. . |
| 0344907 | 12/1989 | European Pat. Off. . |
| 0350291 | 1/1990 | European Pat. Off. . |
| 0370720 | 5/1990 | European Pat. Off. . |
| 2845643 | 4/1980 | Germany . |
| 3042229 | 5/1982 | Germany . |
| 3242870 | 6/1983 | Germany . |
| 1199498 | 6/1970 | United Kingdom . |
| 2019219 | 10/1979 | United Kingdom . |
| 2063679 | 6/1981 | United Kingdom . |

Primary Examiner—John G. Weiss

[57] ABSTRACT

Valve assembly for sealed reception of an elongated object, which includes a valve body defining at least one opening configured and dimensioned to permit entry of the elongated object, a valve member formed of a resilient material and defining an aperture in general alignment with the opening of the valve body, the aperture being configured and dimensioned such that insertion of the object into the aperture causes the resilient material defining the aperture to resiliently engage the outer surface of the object in a substantially fluid tight manner and a manually rotatable control mechanism associated with the valve member to selectively open and close the aperture to permit entry of the object therethrough.

31 Claims, 7 Drawing Sheets

U.S. PATENT DOCUMENTS

| | | | |
|---|---|---|---|
| 4,813,938 | 3/1989 | Raulerson | 604/167 |
| 4,842,591 | 6/1989 | Luther | 604/167 |
| 4,857,062 | 8/1989 | Russell | 604/256 |
| 4,874,377 | 10/1989 | Newgard et al. | 604/167 |
| 4,895,346 | 1/1990 | Steigerwald | 251/149.1 |
| 4,909,798 | 3/1990 | Fleischhacker et al. | 604/167 |
| 4,917,668 | 4/1990 | Haindl | 604/167 |
| 4,929,235 | 5/1990 | Merry et al. | 604/167 |
| 4,935,010 | 6/1990 | Cox et al. | 604/167 |
| 4,960,259 | 10/1990 | Sunnanvader et al. | 251/7 |
| 4,960,412 | 10/1990 | Fink | 604/167 |
| 4,966,588 | 10/1990 | Rayman et al. | 604/167 |
| 4,978,341 | 12/1990 | Niederhauser | 604/167 |
| 5,000,745 | 3/1991 | Guest et al. | 604/167 |
| 5,006,114 | 4/1991 | Rogers et al. | 604/167 |
| 5,009,391 | 4/1991 | Steigerwald | 251/149.1 |
| 5,053,014 | 10/1991 | Van Heugten | 604/167 |
| 5,098,393 | 3/1992 | Amplatz et al. | 604/167 |
| 5,112,321 | 5/1992 | Hilterbrandt | 604/264 |
| 5,127,626 | 7/1992 | Hilal et al. | 251/149.1 |
| 5,161,773 | 11/1992 | Tower | 604/167 |
| 5,180,373 | 1/1993 | Green et al. | 604/256 |
| 5,197,955 | 3/1993 | Stephens et al. | 604/167 |
| 5,205,831 | 4/1993 | Ryan et al. | 604/167 |
| 5,209,737 | 5/1993 | Ritchart et al. | 604/167 |
| 5,256,150 | 10/1993 | Quiachon et al. | 604/167 |

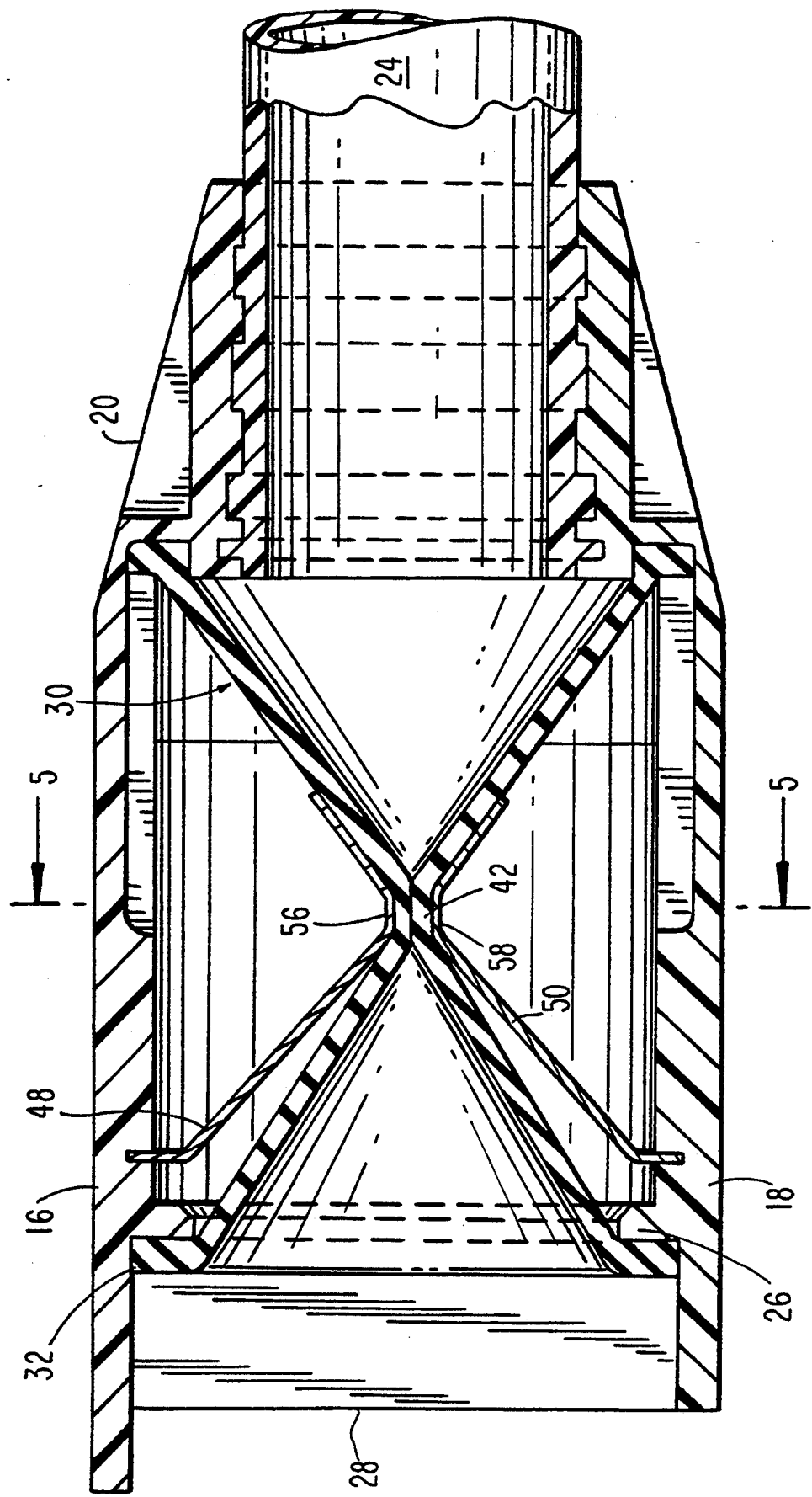

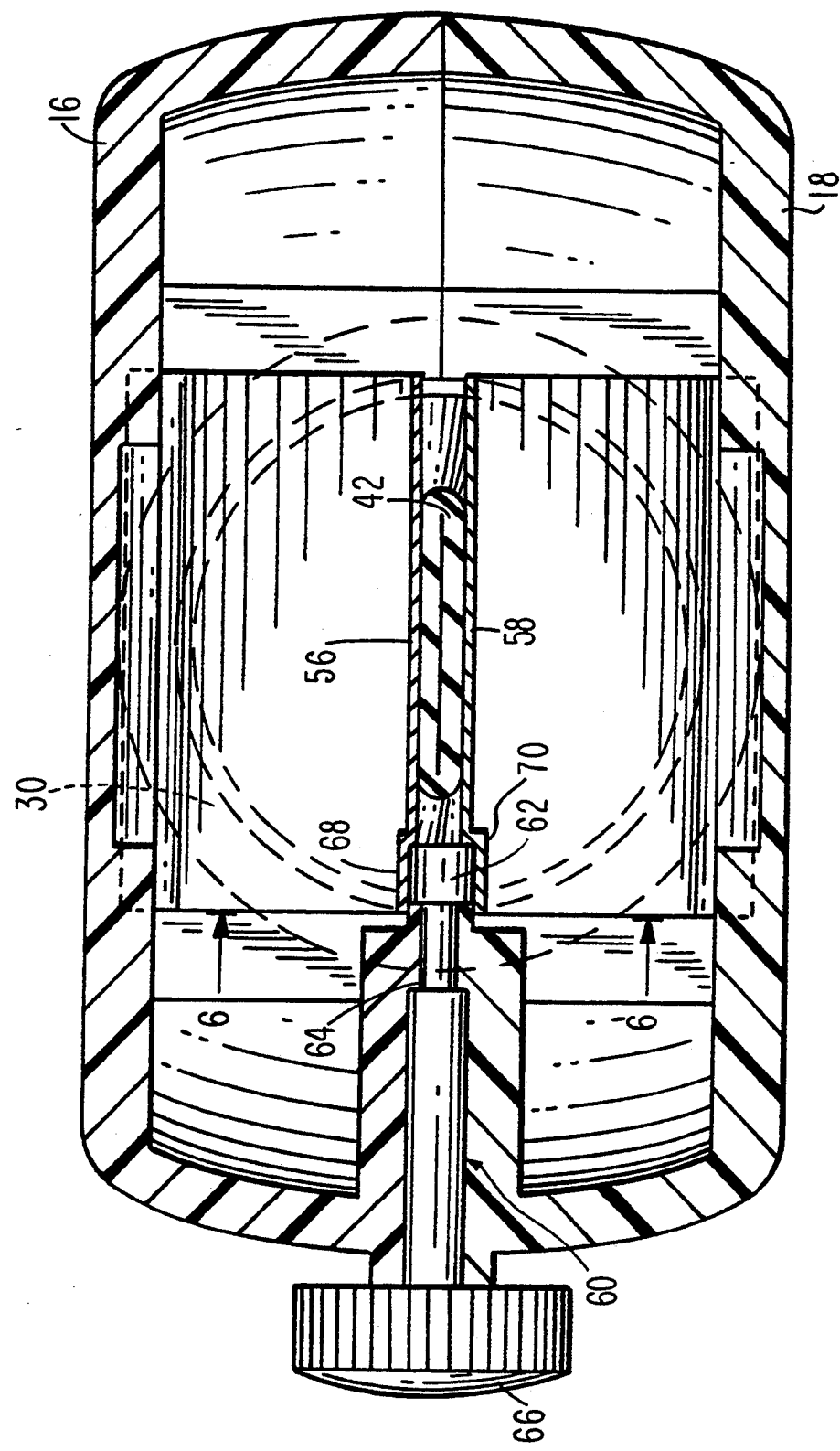

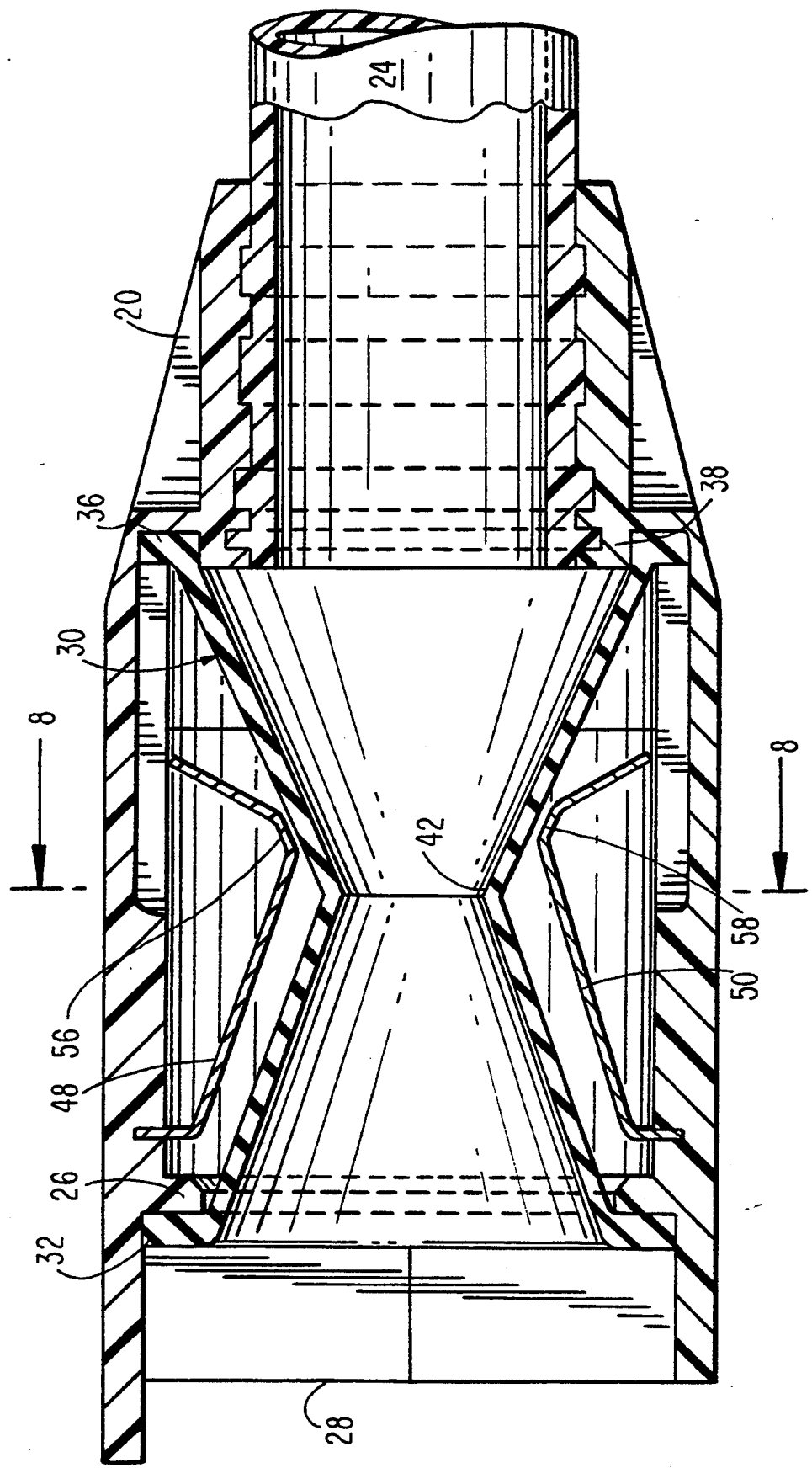

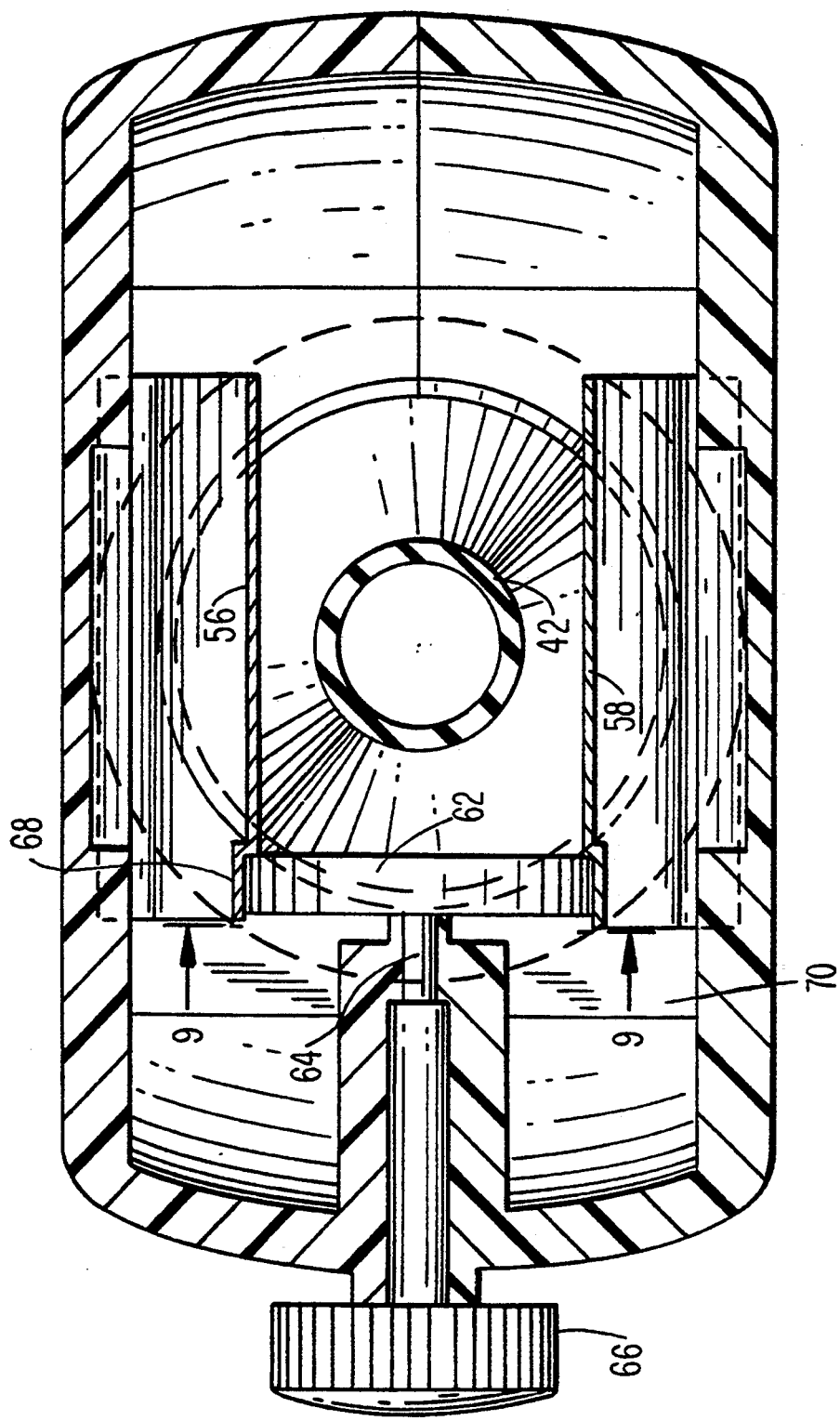

TROCAR SEAL SYSTEM

BACKGROUND OF THE INVENTION

1. Field Of The Invention

This invention relates to valve systems of the type adapted to allow the introduction of a surgical instrument into a patient's body. In particular, the invention is applicable to a cannula assembly and the like wherein a cannula extends from a valve assembly and is intended for insertion into a patient's body and an instrument is inserted into the patient's body through the cannula.

2. Background Of The Prior Art

Minimally invasive surgical procedures involve the introduction of surgical instruments into the body through small incisions and/or cannulas or trocar sleeves. Minimally invasive surgical procedures generally require that any instrumentation inserted into the body be sealed, i.e. provisions must be made to ensure that gases do not enter or exit the body through the incision or trocar sleeve as, for example, in surgical procedures in which the surgical region is insufflated. Moreover, minimally invasive surgical procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system comprised of a cannula assembly and a trocar. A cannula assembly is formed of a cannula or trocar sleeve attached to a valve assembly which is adapted to maintain a seal across the opening of the valve assembly. Since the cannula is in direct communication with the internal portion of the valve assembly, insertion of the cannula into an opening in the patient's body so as to reach the inner abdominal cavity should be adapted to maintain a fluid tight interface between the abdominal cavity and the outside atmosphere.

Since minimally invasive surgical procedures in the abdominal cavity of the body require insufflating gases to raise the cavity wall away from vital organs, the procedure is usually initiated by use of a Verres needle through which a gas is introduced into the body cavity. Thereafter, a trocar, which is a sharp pointed instrument, is inserted into the cannula assembly and used to puncture the peritoneum, i.e. the inner lining of the abdominal cavity wall. The gas provides a slight pressure which raises the wall surface of the peritoneum away from the vital organs, thereby avoiding unnecessary contact with the organs by the instruments inserted into the cannula. This procedure also provides the surgeon with an adequate region in which to operate. Laparoscopic or endoscopic surgical instruments may then be inserted through the cannula to perform surgery within the abdominal cavity or other body portion. The cannula is also utilized for introducing tubes into the body as for drainage purposes or the like.

In view of the need to maintain the atmospheric integrity of the inner area of the cavity, a valve assembly which permits introduction of a trocar or any surgical instrument and which permits selective communication of the inner atmosphere of the cavity with the outside atmosphere is desirable. In this regard, there have been a number of attempts in the prior art to provide such atmospheric integrity.

U.S. Pat. No. 5,180,373 to Green et at. discloses a unique valve assembly which may be incorporated into a cannula assembly or utilized in combination with any type of tubular member for introduction into the body of a patient while permitting introduction of instruments into the body. The assembly disclosed in the Green et at. '373 patent includes a first valve formed of a resilient material and defining an aperture for reception of the object and a second valve positioned adjacent and distal of the first valve in general alignment therewith and defining an aperture in general alignment with the aperture of the first valve. A pair of manually operable clamps is provided to selectively permit the aperture of the second valve to be opened or closed so as to permit entry of the object such that the object first passes through the first valve and then the second valve prior to entry into the patient's body. The manually operable clamps enable the surgeon to selectively open or close the second valve in sequence and in a manner which positively retains the desired interface between the atmosphere on the inlet side of the valve assembly and the atmosphere outside the valve assembly.

Although the valve assembly disclosed in the Green et at. '373 patent is effective for its intended purpose, the present invention is directed to another unique valve assembly for use in combination with a cannula assembly whereby opening of the valve mechanism for permitting entry of the surgical instrument may be readily achieved with an enhanced degree of control, i.e., by the rotation of a single control knob.

SUMMARY OF THE INVENTION

The present invention is directed to a valve assembly for sealed reception of an elongated object, which comprises a valve body defining at least one opening configured and dimensioned to permit entry of the elongated object, a valve member formed of a resilient material and defining an aperture in general alignment with the opening of the valve body wherein the aperture is configured and dimensioned such that insertion of the object into the aperture causes the resilient material defining the aperture to resiliently engage the outer surface of the object in a substantially fluid fight manner, and manually rotatable control means associated with the valve member to selectively open and close the aperture to permit entry of the object therethrough.

The objects contemplated are surgical instruments such as clip appliers, dissectors, graspers, laser and electrocautery devices, drainage or fluid introduction tubes or the like. The valve body includes a neck which extends distally of the distal end thereof and which defines an opening communicating with the interior of the valve body. Further, the distally extending neck of the valve body is adapted to receive a tubular cannula such that the cannula extends distally of the valve body.

In a preferred embodiment, the valve member is generally elongated and defines a proximal inlet portion, a distal outlet portion and an intermediate portion disposed between the inlet and outlet portions. The intermediate portion is capable of collapsing from a generally open position to a substantially closed fluid-tight position in the absence of the elongated object. Lever means is provided and positioned to engage the intermediate portion of the valve member and to collapse the intermediate portion such that the valve member assumes the substantially closed fluid fight position. The preferred lever means comprises a pair of opposed resilient lever members connected to respective lower and upper interior surfaces of the valve body. The lever members are resiliently biased towards each other and positioned to engage opposed surfaces of the intermediate portion of the valve member and collapse the intermediate portion to a configuration whereby the aperture is substantially closed.

The manually rotatable control means includes camming means which is positioned and adapted to engage the opposed levers and displace the levers away from the intermediate portion of the valve member to permit the valve member to assume the generally open position. The camming means is mounted for rotational movement between a first position corresponding to the substantially closed position of the valve member and a second position corresponding to the generally open position of the valve member. The preferred camming means comprises a generally elliptical-shaped camming member defining a major axis greater in dimension than its minor axis. The camming member is mounted at its center to a rotatable rod, whereby rotational movement of the rotatable rod causes corresponding rotational movement of the camming member between the first and second positions. The camming member is positioned between the pair of opposed levers such that rotation thereof to the second position causes engagement with the pair of opposed levers and movement of the levers in a direction away from each other so as to be disengaged from the intermediate portion of the valve member to permit the valve member to assume the generally open position. The rotatable rod is preferably connected to a control knob which is manually rotatable by engagement by the user's fingers.

The present invention is also directed to a cannula and trocar assembly for puncturing a patient's body wall for the introduction of elongated objects such as surgical instruments or the like into the body of a patient while maintaining a substantial fluid fight seal between internal body portions and the outside atmosphere. The assembly comprises a valve housing having an inlet opening at the proximal end and an outlet opening at the distal end, with the distal end opening having a tubular cannula extending distally therefrom. A trocar is positioned within the valve housing and the cannula. Thereafter, the trocar is removed and elongated objects such as surgical instruments or the like may be introduced into the patient's body through the valve assembly and cannula as described hereinabove.

BRIEF DESCRIPTION OF THE PREFERRED EMBODIMENT

The preferred embodiment of the invention is described hereinbelow with reference to the drawings wherein:

FIG. 4 is a cross-sectional view of the valve assembly taken along the lines 4—4 of FIG. 3;

FIG. 5 is a cross-sectional view of the valve assembly taken along the lines 5—5 of FIG. 4;

FIG. 7 is a cross-sectional view similar to FIG. 4 illustrating the resilient valve member in a generally open position with the lever members biased away from the valve member;

FIG. 8 is a cross-sectional view taken along the lines 8—8 of FIG. 7 further illustrating the generally open position of the valve member.

DETAILED DESCRIPTION OF THE PREFERRED EMBODIMENT(S)

The present invention contemplates the introduction into a patient's body of all types of surgical instruments including clip appliers, lasers, photographic devices, tubes, etc. All such objects are referred to herein as "instruments".

Figure 1:
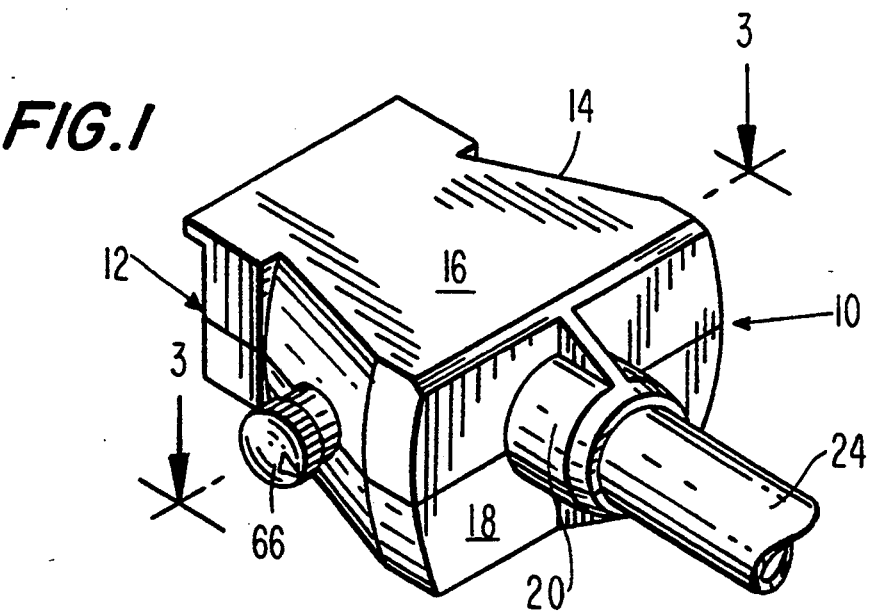
FIG. 1 is a partial perspective view of a cannula assembly incorporating the novel valve assembly constructed according to the present invention.
Figure 6:
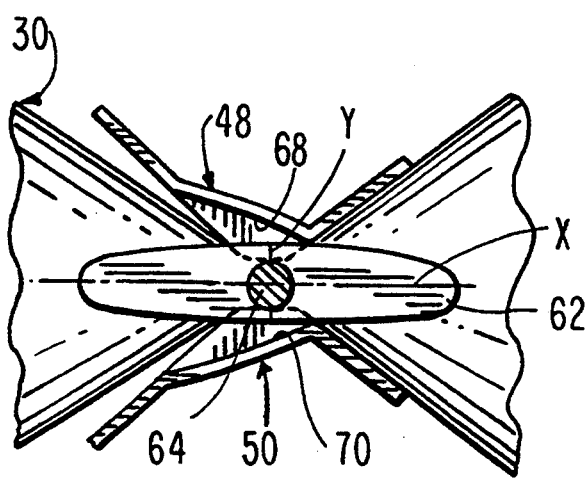
FIG. 6 is an enlarged partial cross-sectional view taken along lines 6—6 of FIG. 5 illustrating the resilient valve member in a generally collapsed condition.
Figure 2:
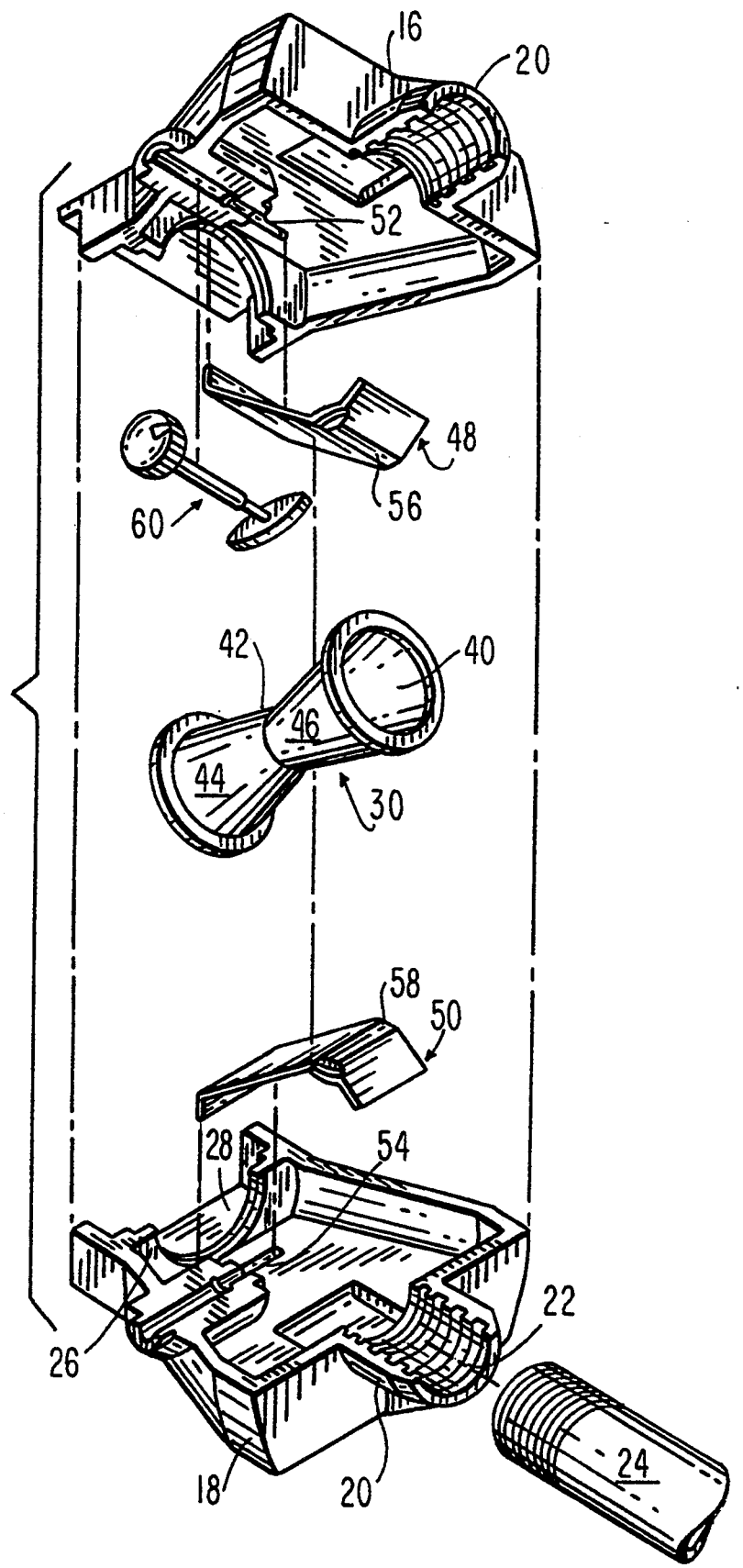
FIG. 2 is a perspective view with parts separated of the valve assembly of FIG. 1.

Referring initially to FIGS. 1 and 2, a cannula assembly 10 is illustrated having incorporated therein the novel valve assembly 12 constructed according to the present invention. Valve assembly 12 includes a valve housing 14 formed of upper housing half section 16 and lower housing half section 18 shown separated in FIG. 2 for convenience of illustration.

The housing half sections 16, 18 are formed of a suitable desirable plastic material such as polycarbonate, polyethylene or the like. One preferred material is LEXAN TM brand polycarbonate manufactured and marketed by General Electric Company, Pittsfield, Mass. The housing half sections 16, 18 are normally attached along the seam by suitable attachment techniques such as adhesive, ultrasonic welding, or the like.

The valve housing 14 includes neck portion 20 at its distal end having an outlet opening 22 dimensioned for reception of an appropriate sheath tube such as cannula 24 to form the cannula assembly 10. The proximal end of valve housing 14 includes partition 26 having annular inlet opening 28. Partition 26 functions in supporting a diaphragm as will be described below.

Figure 3:
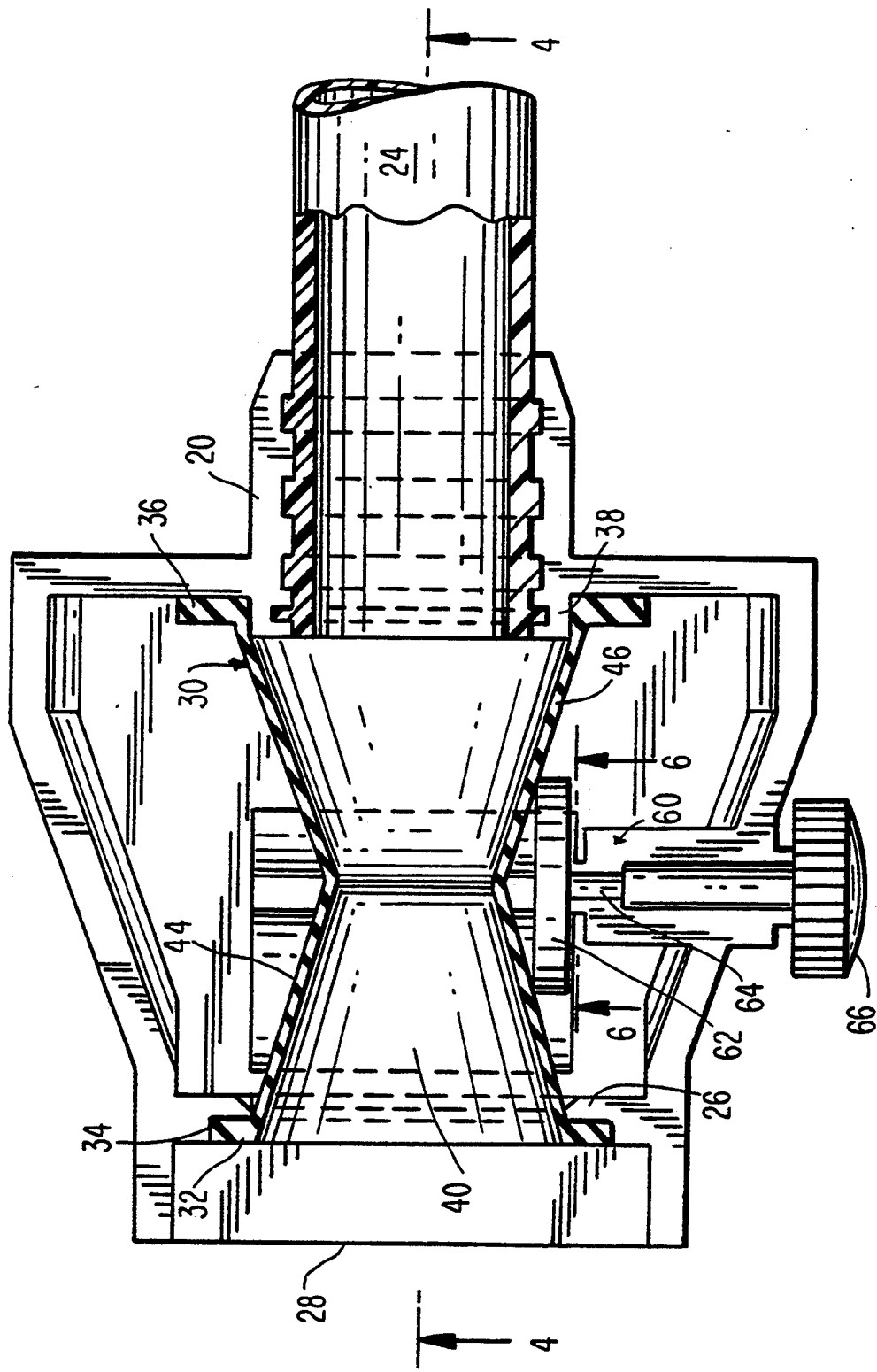
FIG. 3 is a cross-sectional view of the valve assembly taken along the lines 3—3 of FIG. 1.

Referring now to FIG. 2, in conjunction with the cross-sectional view of FIG. 3, the novel inner valve assembly of the present invention will be described. Diaphragm 30 is generally elongated in shape and extends longitudinally through valve housing 14 between inlet opening 28 and outlet opening 22. The proximal end of the diaphragm 30 includes a circular flange 32 which fits tightly by a snap fit within a correspondingly dimensioned annular recess 34 formed on the proximal side of partition 26. The distal end of diaphragm 30 also includes a circular flange 36 which fits tightly about the periphery of the proximal end portion 38 of neck 20, which extends within the interior of the valve housing 14 as best shown in FIG. 3.

Diaphragm 30 defines a longitudinal bore or aperture 40 for sealing reception of an instrument as will be described. The diameter of the bore 40 gradually decreases towards the midportion 42 of the diaphragm 30 to form the hourglass configuration of the diaphragm as shown in FIG. 2. The dimension of bore 40 at constricted midportion 42 of the diaphragm is less than or equal to the outer diameter of the instrument intended for entry into the inlet opening 28 of the valve assembly 12. Diaphragm 30 is fabricated from an elastomeric material such as synthetic or natural rubber which is preferably sufficiently resilient to accommodate and provide a fluid seal with instruments of varying diameters, e.g., diameter of from about 5 mm to about 10 mm. The generally tapering configuration of proximal portion 44 of elongated diaphragm 30 facilitates entry of the instrument into the diaphragm. Similarly the generally tapering configuration of the distal portion 46 facilitates passage of the object through the diaphragm 30 and into the cannula 24.

Referring now to FIG. 2, in conjunction with FIG. 4, a pair of opposed resilient levers 48, 50 are connected at their proximal end portions to the interior surfaces of upper and lower housing half sections 16, 18 respectively. In particular, the proximal end portions of each lever 48, 50 are snugly received within correspondingly dimensioned and positioned recesses 52, 54 (FIG. 2) formed in the respective interior surfaces of the upper and lower half sections 16, 18 to mount levers 46, 48 to the valve housing 14. Other methods for mounting levers 48, 50 may be readily determined by one skilled in the art. Levers 48, 50 extend generally longitudinally within valve housing 14 and have disposed therebetween diaphragm 30. Levers 48, 50 are normally biased in a direction towards each other and the central axis defined by valve housing 14 to engage opposed outer surfaces of the diaphragm 30 and collapse the diaphragm as best shown in FIG. 4. The levers are preferably fabricated from a resilient material such as stainless steel or the like.

Referring now to FIGS. 2 and 4, in conjunction with the cross sectional view of FIG. 5, levers 48, 50 define planar engaging surfaces 56, 58, respectively, which engage the constricted midportion 42 of diaphragm 30 to collapse this portion to form a substantially fluid tight seal between the proximal and distal ends of the diaphragm in the absence of a surgical instrument. The widths of engaging surfaces 56, 58 of levers 48, 50 are preferably greater than the diameter of constricted midportion 42 of diaphragm 30 as shown in FIG. 5 to ensure the bore 40 is completely closed in the manner depicted in the Fig.

Referring now to FIGS. 2, 3, 5 and 6, the unique camming mechanism for opening the diaphragm 30 to permit the introduction of a surgical instrument through valve assembly 12 will now be described. Camming mechanism, identified generally by reference numeral 60, includes camming member 62, camming rod 64 and control knob 66. Camming member 62 is generally elliptical in shape having a major axis X greater in dimension than its minor axis Y. (FIG. 6) Camming member 62 is disposed between opposed levers 48, 50 and engagingly contacts camming surfaces 68, 70 formed at the peripheral potions of levers 48, 50 in the manner shown in FIGS. 5 and 6. Camming rod 64 is securely connected to camming member 62 and extends to the exterior of valve housing 14 where it is connected to control knob 66. Control knob 66 possesses a knurled surface to facilitate grasping by the surgeon. As will become appreciated from the description provided below, rotation of the control knob 66 causes corresponding rotation of camming rod 64 and camming member 62, which, in ram, causes displacement of the levers 48, 50 in a direction away from the central axis of valve housing 14 and from each other to permit elongated diaphragm 30 to assume its normal open position.

The operation of the valve assembly will now be described. The valve assembly is intended to be supplied as part of a cannula assembly, having a distal cannula tube 24 as shown in FIGS. 1 and 2. A trocar which is a sharp pointed instrument is usually fitted within a cannula assembly. The trocar is used to insert the cannula into a body cavity by first piercing the cavity wall (i.e., the peritoneum) and then introducing the cannula into the formed incision. Thereafter, the trocar is removed, permitting insertion of instruments into the patient's body through the cannula 24 to perform the desired procedure. Thus, the significance of providing control to the surgeon of the sealed state of the opening in the cannula assembly cannot be overemphasized. Such opening will ultimately control the exposure between the internal pan of the body cavity and the outside atmosphere. For laparoscopic procedures, the valve assembly will preserve the state of insufflation of the peritoneum during the surgical procedure.

During the removal of the trocar from the cannula assembly, diaphragm 30 closes automatically under the action of resilient levers 48, 50 which engage midportion 42 of the diaphragm and collapse the diaphragm as depicted in FIGS. 4 and 5. The surgeon may then insert an instrument into the body cavity by first inserting the instrument into inlet opening 28 (FIG. 3) at the proximal end of valve housing 14 and then rotating control knob 66 to open diaphragm 30 to permit passage of the instrument through the valve housing.

Figure 9:
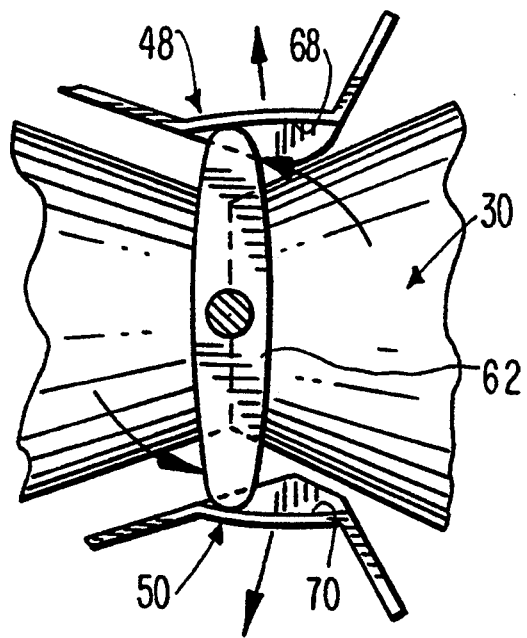
FIG. 9 is an enlarged partial cross-sectional view taken along the lines 9—9 of FIG. 8 illustrating the camming mechanism rotated in a manner to engage and displace the lever members from their engagement with the valve member.

In the preferred embodiment, control knob 66 is rotated in a counterclockwise direction which causes corresponding counterclockwise rotational movement of rod 64 and camming member 62. As depicted in FIG. 9, as camming member 62 rotates in the counterclockwise direction shown by the directional arrows, the elongated portion defined by its major axis X engages camming surfaces 68, 70 of levers 48, 50 and forces the levers 48, 50 away from each other (as shown by the indicator arrows) towards their respective upper and lower half sections 16, 18. The particular slightly arcuate dimensions of camming surfaces 68, 70 accommodate the curved surfaces of camming member 62 during rotation of the camming member to ensure smooth movement thereof. Continued rotational movement causes camming member 62 to lift levers 48, 50 from their engagement with constricted midportion 42 of diaphragm 30 to permit the diaphragm 30 to assume its normal open position, thus enabling the passage of an instrument through diaphragm 30. FIGS. 7 and 8 illustrate diaphragm 30 in the open position with camming member 62 rotated to engage camming surfaces 68, 70 of levers 48, 50 so as to displace the levers away from the diaphragm.

The instrument may then be passed through diaphragm 30 where the constricted bore or office defined at midportion 42 of diaphragm 30 forms a fluid tight seal about the periphery of the instrument, which, accordingly seals the inner body cavity from the outside atmosphere. This seal is provided by the resilient property of the stretched elastomeric material surrounding the orifice. Manipulation of the instrument in any direction will not affect the seal, since the elastomeric material defining the opening will conform to the movements of the instrument and assume an elliptical or other shape necessary to maintain contact.

The constricted bore or orifice defined at midportion 42 of diaphragm 30 is preferably dimensioned between 3 and 15 mm to accommodate laparoscopic and endoscopic instruments such as clip appliers, laser tubes, photographic instruments, tubes or the like. However, depending upon need or application this dimensional range may be varied to accommodate any particular instrument.

The opening of bore is always under the surgeon's control through control knob 62 and is adapted to be automatically actuated to the closed condition under action of resilient levers 48, 50 when the surgeon removes the instrument or other object from the valve assembly. Further, manipulation of the instrument does not affect the shape of diaphragm 30, or the sealing contact of the inner wall of the diaphragm with the instruments because the diaphragm is sufficiently flexible and resilient to maintain contact with the surface of the instrument. Thus, during the entire sequence, the integrity of the seal between the inside of the body cavity and the outside atmosphere is clearly maintained.

To the extent not already indicated, it also will be understood by those of ordinary skill in the art that any one of the various specific embodiments herein described and illustrated may be further modified to incorporate features shown in other of the specific embodiments.

The invention in its broader aspects therefor is not limited to the specific embodiments herein shown and described but departures may be made therefrom within the scope of the accompanying claims without departing from the principles of the invention and without sacrificing its chief advantages.

What is claimed is:

1. Valve assembly for sealed reception of an elongated object, which comprises:
   (a) valve body defining at least one opening configured and dimensioned to permit entry of the elongated object;
   (b) valve member formed of a resilient material and defining an aperture in general alignment with said at least one opening of said valve body, said aperture being configured and dimensioned such that insertion of the object into said aperture causes the resilient material defining said aperture to resiliently engage the outer surface of the object in a substantially fluid tight manner, a portion of Said valve member capable of collapsing from a generally open position to a substantially closed fluid tight position in the absence of the elongated object;
   (c) at least one lever member disposed within said valve body and positioned adjacent said valve body, said at least one lever member normally biased to engage at least a portion of said valve member and collapse said valve portion such that said valve member assumes said substantially closed fluid tight position;
   (d) manually rotatable control means associated with said valve member to selectively open and close said aperture to permit entry of the object therethrough, said control means including a camming member rotatable about an axis of rotation and having camming surfaces dimensioned to engage and displace said at least one lever member upon rotation of said camming member to permit said valve member to assume said generally open position.

2. Valve assembly according to claim 1 wherein the object is a surgical instrument.

3. Valve assembly according to claim 2 wherein said valve member is generally elongated and defines a proximal inlet portion, a distal outlet portion and an intermediate portion disposed between said inlet and outlet portions.

4. Valve assembly according to claim 3 wherein said intermediate portion of said valve member is capable of collapsing from said generally open position to said substantially closed fluid tight position in the absence of the elongated object.

5. Valve assembly according to claim 4 wherein said at least one lever member comprises a pair of opposed resilient lever members connected to respective lower and upper interior surfaces of said valve body, said lever members resiliently biased towards each other and positioned to engage opposed surfaces of said intermediate portion and collapse said intermediate portion to a configuration whereby said aperture is substantially closed.

6. Valve assembly according to claim 5 wherein said camming member is positioned and adapted to engage said opposed levers and displace said levers away from said intermediate portion of said valve member upon rotation of said camming member to permit said valve member to assume the generally open position.

7. Valve assembly according to claim 6 wherein said camming member is mounted for rotational movement between a first position corresponding to said substantially closed position of said valve member and a second position corresponding to Said generally open position of said valve member.

8. Valve assembly according to claim 7 wherein said camming member is generally elliptical-shaped defining a major axis greater in dimension than its minor axis.

9. Valve assembly according to claim 8 wherein said camming member is mounted at its center to a rotatable rod, whereby rotational movement of said rotatable rod causes rotational movement of said camming member between said first and second positions.

10. Valve assembly according to claim 9 wherein said camming member is positioned between said pair of opposed levers such that rotation thereof to said second position causes engagement with said pair of opposed levers and movement of said levers in a direction away from each other and disengaged with said intermediate portion of said valve member to permit said valve member to assume the generally open position.

11. Valve assembly according to claim 10 wherein said rotatable rod is connected to a control knob which is manually rotatable by engagement by the user's fingers.

12. Valve assembly according to claim 11 wherein said control knob includes an irregular surface portion to facilitate engagement by the user's fingers.

13. Valve assembly according to claim 10 wherein said major axis of said camming member is angularly offset relative to a longitudinal axis defined by said valve body when said camming means is in said second position thereof.

14. Valve assembly according to claim 13 wherein said major axis of said camming member is generally transverse to said longitudinal axis defined by said valve body when said camming means is in said second position thereof.

15. Valve assembly according to claim 14 wherein said major axis of said camming member is generally parallel to said longitudinal axis of said valve body when said camming means is in said first position thereof.

16. Valve assembly according to claim 1 wherein said valve body comprises a neck extending distally of a distal end thereof, said neck defining an opening communicating with the interior of said valve body.

17. Valve assembly according to claim 16 Wherein said distally extending neck of said valve body is adapted to receive a tubular member such that said tubular member extends distally of said valve body.

18. Valve assembly according to claim 17 wherein said valve body is a two piece valve housing assembled at a medial interface.

19. Valve assembly according to claim 18 wherein said valve housing is constructed of a relatively rigid plastic material such as polycarbonate, polyethylene or the like.

20. Valve assembly for introduction of an elongated object into a patient's body while maintaining the atmospheric integrity therein, which comprises:
   (a) valve body defining a longitudinal axis and having a proximal inlet opening and a distal outlet opening;
   (b) elongated valve member formed of a flexible elastomeric resilient material and defining a longitudinal bore therethrough for reception of the object, said valve member adapted to engage and conform to the outer surfaces of the elongated object received therewithin in a substantially fluid tight manner;
   (c) first and second opposed levers connected at first end portions thereof to respective upper and lower interior surfaces of said valve body, said first and second opposed levers positioned and dimensioned to bias said flexible valve member to a configuration whereby said bore is substantially closed to form a fluid tight seal prior to inserting the object therethrough; and
   (d) manually rotatable control means to selectively open said bore of said valve member to permit passage of the object therethrough, said control means including a camming member at least partially disposed between said first and second opposed levers, said camming member mounted for rotational movement and having camming surfaces dimensioned to displace said opposed levers upon rotational movement of said camming member to permit said longitudinal bore of said resilient valve member to assume a generally open position, said control means actuated by a single control knob.

21. Valve assembly according to claim 20 wherein at least a portion of said resilient valve member is positioned between said first and second opposed levers.

22. Valve assembly according to claim 21 wherein said first and second opposed levers are resiliently biased towards said longitudinal axis of said valve body and are positioned and oriented to engage opposed surface portions of said resilient vane member in a manner to collapse at least a portion of said valve member to form a substantially fluid tight seal.

23. Valve assembly according to claim 22 wherein said camming member is generally elliptical-shaped and defines a major axis greater in dimension than a minor axis, said camming member adapted to rotate between first and second positions, said first position corresponding to a substantially closed position of said resilient valve member wherein said major axis is generally parallel to said longitudinal axis of said valve body, said second position corresponding to a generally oven position of said resilient valve member wherein said major axis is angularly offset relative to said longitudinal axis.

24. Valve assembly for sealed reception of an elongated object into a patient's body, which comprises:
   a) valve body defining a longitudinal axis and having means configured and dimensioned to permit entry of the object;
   b) elongated flexible resilient valve member defining a longitudinal bore and having a constricted intermediate portion, said bore in general alignment with said entry means and configured and dimensioned such that insertion of the object into said bore will cause the resilient material defining said constricted intermediate portion to resiliently engage the outer surface of the object in a substantially fluid tight manner;
   c) at least one member to bias said intermediate portion of said valve member to a configuration whereby said bore is substantially closed to form a fluid tight seal; and
   d) manually operative means to open said bore of said valve member, said operative means including a camming member rotatable about an axis substantially transverse to said longitudinal axis of said valve body, said camming member having camming surfaces positioned to engage said at least one member upon rotation thereof in a first direction to displace said at least one member to permit said bore of said valve member to open to permit insertion of the object therethrough.

25. Valve assembly according to claim 24 wherein said valve member includes a proximal potion which tapers outwardly from said constricted intermediate portion to facilitate entry of an elongated object within said orifice.

26. Valve assembly according to claim 25 wherein said valve member includes a distal potion which tapers outwardly from said intermediate portion to facilitate passage of the elongated object through said valve member.

27. Valve assembly according to claim 26 wherein said manually operative means comprises a rotatable control knob rotatably mounted to said valve body and connected to said Camming member such that said camming member is rotatable therewith, said control knob adapted to rotate between first and second positions, said first position corresponding to a substantially closed position of said bore of said valve member, said 28. A cannula and trocar assembly for puncturing a patient's body wall for the introduction of elongated objects such as surgical instruments or the like into the body of a patient while maintaining a substantial fluid tight seal between internal body portions and the outside atmosphere, which comprises:
   a) valve housing having an inlet opening at the proximal end and an outlet opening at the distal end, said distal end opening having a tubular cannula extending distally therefrom;
   b) trocar positioned within said valve housing and said cannula;
   c) elongated valve means of resilient material in general alignment with said inlet opening of said valve housing, said valve means having a longitudinal bore dimensioned for reception of said trocar or the object in a manner such that resilient material surrounding said bore engages the surfaces of the trocar or the object to provide a substantial fluid tight seal which prevents passage of fluids past the interface;

d) a pair of opposed lever members positioned within said valve housing on opposed sides of at least an intermediate portion of said elongated valve means, said lever members resiliently biased towards each other and oriented to engage at least said intermediate portion of said elongated valve means and collapse said intermediate portion to a configuration whereby said bore is substantially closed to form a fluid tight seal prior to positioning the object therein; and e) manually rotatable control means adapted to selectively separate said lever members in a manner to open said bore of said elongated valve means to permit passage of the object therethrough, said control means including a camming member rotatably mounted about an axis of rotation, said camming member disposed between said opposed levers and dimensioned to engage and move said lever members away from each other upon rotation of said camming member to permit said bore to open to receive said trocar or the object.

29. Valve assembly for sealed reception of an elongated object, which comprises:

valve body defining at least one opening configured and dimensioned to permit entry of the object;

elongated valve member formed of a flexible elastomeric resilient material and defining a longitudinal bore therethrough for reception of the object, said valve member adapted to engage and conform to the outer surface of the elongated object received therewithin in a substantially fluid fight manner;

first and second opposed levers connected at first end portions thereof to respective upper and lower interior surfaces of said valve body, said first and second opposed levers resiliently biased towards each other and positioned to engage opposed surfaces of an intermediate portion of said valve member and collapse said intermediate portion to a configuration whereby said bore is substantially closed; and means for selectively opening said bore of said valve member to permit passage of the object therethrough, said opening means including a camming member disposed between said first and second opposed levers and being rotatable about an axis of rotation between first and second positions, said first position corresponding to a substantially closed position of said valve member, said second position corresponding to a generally open position of said valve member.

30. Valve assembly according to claim 29 wherein said camming member is rotatable about its center.

31. Valve assembly according to claim 30 wherein said camming member is connected to a manually rotatable control knob wherein rotational movement of said control knob causes rotational movement of said camming member between said first and second positions.

* * * * *